United States Patent [19]

Munk

[11] 4,006,990
[45] Feb. 8, 1977

[54] CONVERGENT LIGHT ILLUMINATED FLOW CELL FOR LIQUID CHROMATOGRAPHY

[75] Inventor: Miner N. Munk, Walnut Creek, Calif.

[73] Assignee: Varian Associates, Palo Alto, Calif.

[22] Filed: Mar. 22, 1976

[21] Appl. No.: 669,136

Related U.S. Application Data

[62] Division of Ser. No. 490,548, July 22, 1974, Pat. No. 3,975,104.

[52] U.S. Cl. .............................. 356/246; 356/201
[51] Int. Cl.² ......................................... G01N 1/10
[58] Field of Search ................... 356/201, 205–208, 356/244, 246, 180, 181; 250/573, 576

[56] References Cited

UNITED STATES PATENTS

| | | | |
|---|---|---|---|
| 2,617,940 | 11/1952 | Giguere | 356/206 |
| 3,263,554 | 8/1966 | Pickels | 356/246 |
| 3,480,369 | 11/1969 | Smytae et al. | 356/201 |
| 3,920,334 | 11/1975 | Steichen et al. | 356/205 |

FOREIGN PATENTS OR APPLICATIONS

| | | | |
|---|---|---|---|
| 624,125 | 12/1935 | Germany | 356/201 |

Primary Examiner—John K. Corbin
Assistant Examiner—Jon W. Henry
Attorney, Agent, or Firm—Stanley Z. Cole; Gerald M. Fisher; John J. Morrissey

[57] ABSTRACT

Single and dual beam flow cells for liquid chromatography that provide good detectability and linear response with small sample volumes. A cylindrical window surrounds the sample flow path to permit focusing convergent light rays through the center of the flow path and along optical paths of equal length through the cell. Optical stops limit the light passing through the cell to convergent rays incident to the window surface. A wide acceptance angle for the rays results in high light transmission and averages variations in light output along the light source. A dual beam flow cell utilizes a common exit for the sample and reference liquids. The flow cells are economically constructed for direct coupling to a chromatographic column by using a standard compression fitting union and can be used in a single wavelength or discrete wavelength detector, or in a spectrophotometer.

4 Claims, 9 Drawing Figures

FIG. 5
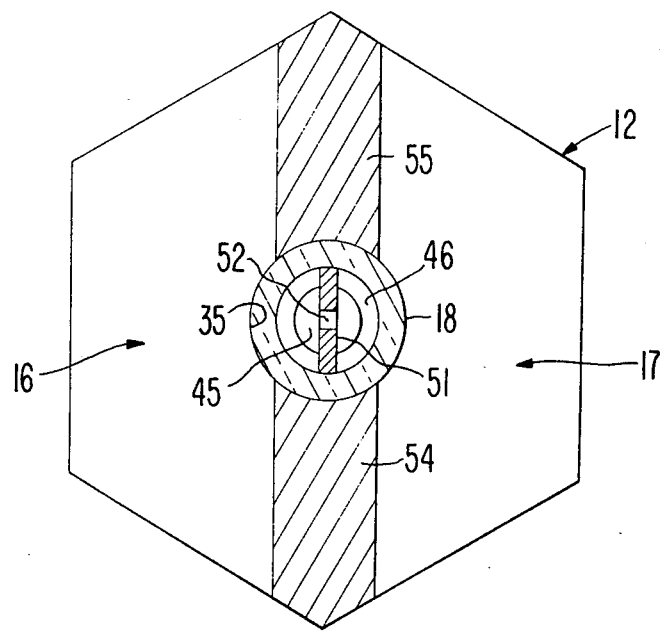
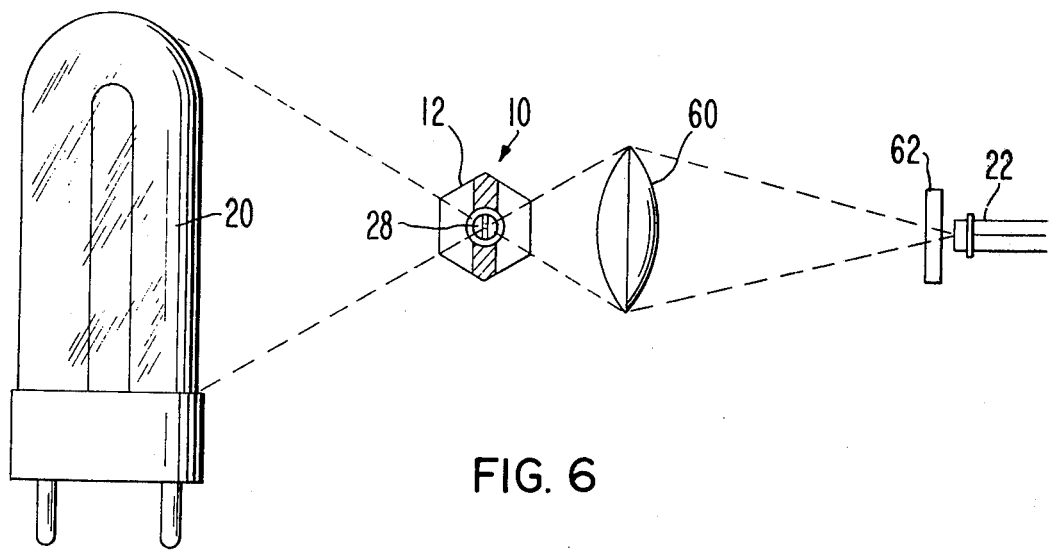
FIG. 6
FIG. 7
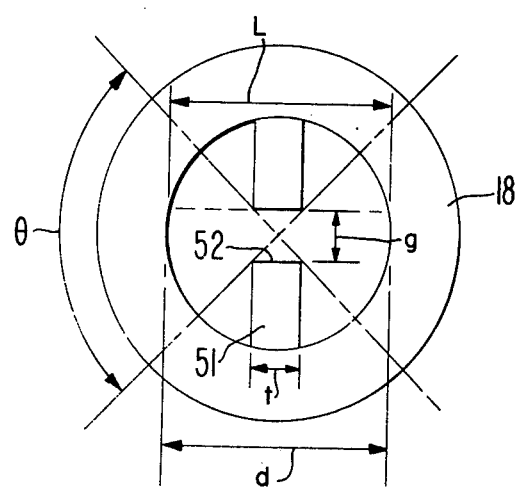

CONVERGENT LIGHT ILLUMINATED FLOW CELL FOR LIQUID CHROMATOGRAPHY

This is a division of application Ser. No. 490,548 filed July 22, 1974 now Pat. No. 3,975,104.

BACKGROUND OF THE INVENTION

1. Field of the Invention

This invention relates to liquid chromatographic detectors and more particularly to improved flow cell constructions for liquid chromatography.

2. Prior Art

A chromatographic detector is a device which supplies an output signal related to the amount or rate of change of the amount of a sample to be detected in the effluent of a chromatographic column. It indicates elution of the separated components of the input substance by the column and provides a measure of the amount of each component. It is usually the most sophisticated and one of the most expensive components in a chromatograph. The majority of high performance liquid chromatograph detectors in use today are UV or visible light absorption and refractive index detectors. Light rays are directed through the sample and the effect of the sample on the rays, e.g., light absorption, is detected by a photocell.

Good detectability, i.e., ability to detect a small sample, is desired so that small samples and small column capacity can be used, resulting in shorter analysis times. Some new, highly efficient, column packing materials have inherent low capacity and require detectors capable of detecting small samples. Also, low sample solubility in the mobile phase may limit the amount of sample available for detection.

With small flow cell volumes, present flow cell geometries offer low light transmission, poor flow geometry, and become expensive to manufacture. Parallel light rays are used with flat or cylindrical cell entry windows. Also, convergent light rays have been used with flat windows, and typically the convergent light rays are focused on the entry window for maximum transmission to the cell. The path lengths of parallel light rays passing through a cylindrical cell differ across the width of the cell. Also, the path lengths of convergent light rays passing through a flow cell with flat entrance and exit windows differ across the area of the flow cell. Since light absorbance is a function of the path length through the cell, the output signal from such cells is nonlinear; that is, the detector response does not change linearly with the amount of sample present. Linearity is desirable because it facilitates quantitation of the results, eliminating the need of functional calibration curves to determine the quantity of the component present.

In particular, there is a need in the prior art for a high light transmission cell with a small aperture to accommodate a small sample for use in high performance liquid chromatography and which affords equal path length for the light rays directed through the cell.

SUMMARY OF THE INVENTION

The present invention provides a flow cell for liquid chromatography that has a small cell volume and that utilizes convergent light rays and a cylindrical window so that the path length for all rays focused on the cell is the same. This arrangement assures high light transmission even though only a small aperture for the light is available, and assures good linearity of the output. A large light acceptance angle is afforded by the present construction; and, when used with a broad light source, the present construction averages any local light intensity fluctuations, thereby enhancing the acceptability of a single beam detector. The present construction can also be used in conjunction with beam condensing lenses in a spectrophotometer without loss of linearity in response.

The flow cell of the present invention is constructed for direct coupling to a chromatograph column, is capable of high pressure and high temperature operation, is chemically inert, and is of versatile construction to facilitate different apertures. Economical fabrication is assured because this cell can be fabricated from a standard compression fitting union without intricate machining.

In one embodiment of this invention, dual beam flow cells are provided with a common exit for both the detection and the reference cells. This allows a compact cell construction and keeps the cells close together for thermal equilibration.

More specifically, the present flow cell construction utilizes a quartz cylindrical window surrounding a small capacity flow passage. Light stops are provided within the window structure and passage to limit the light passing through the cell to convergent rays, but at the same time providing a large acceptance angle for the rays. With this construction, rays transmitted through the flow cell are of a high intensity notwithstanding the small aperture necessitated by the size of the flow passage. The cell is housed in a compression fitting union directly coupled to the chromatographic column. Where a reference cell is desired to factor out solvent effects and light fluctuations, a feature of this invention includes the axial alignment of two flow cell passages that are fed from opposite directions and which discharge into a common zone centrally between the two passages. The flow is then discharged through a single port in a direction perpendicular to the flow through the cells.

It is an object of this invention to provide a convergent light flow cell that is compact, inexpensive and capable of high performance, and which is particularly well suited for high performance liquid chromatography.

Other objects, features and advantages of the present invention will become more apparent from the detailed description that follows, when considered in connection with the accompanying drawings.

BRIEF DESCRIPTION OF THE DRAWINGS

FIG. 5 is a transverse section taken along the line 5—5 of FIG. 2;

FIG. 6 is an optical schematic view of a liquid chromatography detector embodying the present invention;

FIG. 7 is a top plan view of a flow cell, diagrammatically indicating the relationship of optical stops and the acceptance angle for light rays;

DETAILED DESCRIPTION OF PREFERRED EMBODIMENTS

Figure 9:
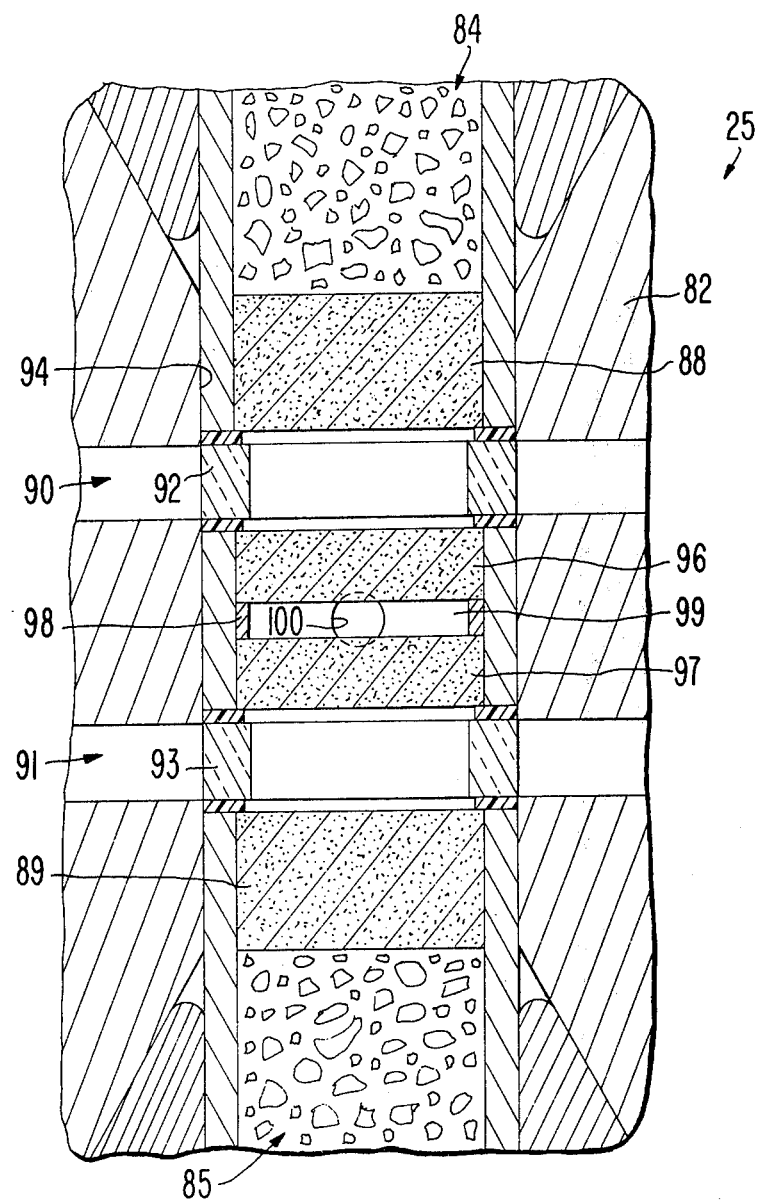
FIG. 9 is a longitudinal sectional view of a dual beam flow cell embodying the present invention.

With reference now to the drawings, a miniature flow cell assembly 10 is shown for a single light beam detector. It is formed from a standard compression fitting union 12 secured to the end of a packed liquid chromatographic column 14. The flow cell assembly has open portions 16, 17 in the union and a cylindrical window 18 through which components of a sample that flows through the columns can be detected. Detection is accomplished through a light source 20 and a photocell 22, as best shown in FIG. 6. Sample components carried by a solvent are separated by the packing in the liquid chromatographic column 14. Because certain sample components absorb light, the presence of the components can be detected by a photocell sensitive to the degree of absorption of light by the components. An output signal from the photocell 22 is related to the amount or rate of change of sample in the column effluent. A dual beam flow cell assembly 25 is shown in FIG. 9, which provides two paths and two windows for light transmission, for measuring and comparing the sample to a standard, and thereby factoring out solvent effects and variations of light intensity of the source. With the basic construction of the various embodiments, a constant length light path and high light transmission is achieved through the flow cell.

A flow cell portion 28 of the assembly 10 is located between adjacent but spaced ends of a tube 29 forming the column 14 and an exit tube 32, and is aligned with the openings 16, 17 formed in the union 12, which are made by cutting slots through the nut portion 34 of the union in a common transverse plane to a depth that intersects a central passage 35 of the union. This is best shown in FIG. 5. The column tube 29 is closely received in one end of the union 12, and the juncture is sealed by a compressible ferrule 36 and a nut 37 threaded to the union. The column 14 contains a packing 39. The lower end of the column receives a porous plug column packing retainer 40 that permits liquid passing through the column packing to enter the flow cell and exit through the exit tube 32. The exit tube 32 is spaced from the plug 40 by the cylindrical quartz window 18. Two Teflon gaskets 42, 43 provide seals on opposite sides or ends of the window 18.

The exit tube 32 tightly fits within the central passage 35 of the union and provides a central passageway 45 downstream from the flow cell portion 28. Optionally, a porous stainless steel plug or the like can be provided at the bottom of the flow cell portion 28 serve as a boundary to the central passageway 45 of the exit tube 32. A reduced diameter cylindrical boss 46 extends from the upper end of the exit tube to tightly be received within one end of the cylindrical window 18. The axial distance between the upper end of the boss 46 and the lower end of the plug 40 defines the flow cell portion 28, within the cylindrical window 18. Two diametrically opposite aligned slots 48, 49 are formed in the boss 46, and receive a plate 51, which extends axially the distance between the boss 46 and the plug 40. A central slot 52 in the plate 51 extends axially the distance between the boss 46 and plug 40, providing a path between opposite sides of the plate, through which light rays can pass when directed through the cylindrical window 18 on one side of the plate 51. The plane of the plate 51 is aligned with two web portions 54, 55 (FIG. 5) of the union 12, that are formed as a result of the cut out portions 16, 17. It will be apparent that these web portions essentially divide the cylindrical window 18 into two cylindrical window segments, one for light input and the other for light output. Other means of forming optical stops will of course be apparent to those skilled in the art, the important feature being the provision of a narrow gap with a wide acceptance angle (assured in the disclosed embodiment by the use of a thin plate 51) in the center of the pathway through the cylindrical flow cell portion 28. A ferrule 56 and nut 57 seal and retain the exit tube in the union.

A general detector arrangement is shown in FIG. 6 of the drawings and includes the lamp 20, in this case an ultraviolet lamp elongated in the direction shown with respect to the orientation of the flow cell assembly 10, and which typically can emit radiation of a prescribed wavelength, such as 254 nm. A lens 60 is positioned to receive diverging rays that pass through the flow cell 28 and to focus them upon the photocell 22. The locations of the lamp 20 and lens 60 are selected relative to the union 12 so that converging rays from the lamp pass through the cut out slot 16 or 17 and emerge through the opposite cut out slot. A UV filter 62 is provided in front of the photocell 22 to limit the rays detected to a prescribed wavelength, and the photocell 22 produces an output signal proportional to the intensity of the rays. The light acceptance angle of the flow cell is controlled by the plate 51, although in some constructions the slots 16, 17 could be a limiting factor. For good results, the acceptance angle should be at least 45° and preferably 90°. In the embodiment shown, the acceptance angle is approximately 90°.

As best shown diagramatically in FIG. 7, a wide acceptance angle $\theta$ is provided as long as the slot width $g$ is not small with respect to the thickness $t$ of the plate 51. This assures that a large quantity of light, i.e., high light intensity, can be received through the relatively narrow slot 52. Within the acceptance angle $\theta$, all rays passing through the cylindrical window 18 and the slot 52 are essentially of equal length through the flow cell. By way of example, with reference to FIG. 7, if the flow cell diameter $d$ is 2.0 mm, and the plate thickness $t$ and slot width $g$ are both equal to 0.5 mm, the minimum light path length L is 1.937 mm or only 3.2% shorter than the maximum length (i.e., diameter $d$) of 2.0 mm. By keeping the width $g$ small, the difference is minimized; and by keeping the thickness $t$ small, the acceptance angle is maximized. In addition, as shown by the schematic diagram of FIG. 6, light converging from the entire length of the ultraviolet lamp 20 will pass through the slot 52, thereby averaging any variations in light that might occur throughout the area of the lamp.

Figure 1:
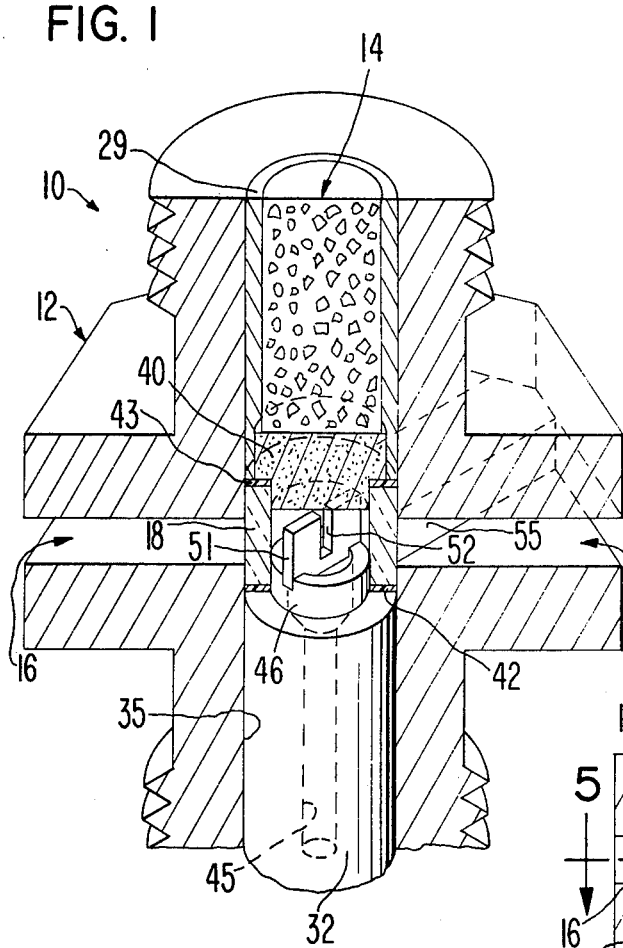
FIG. 1 is a partial perspective view, with parts cut away, showing one embodiment of a flow cell incorporating the present invention.
Figure 2:
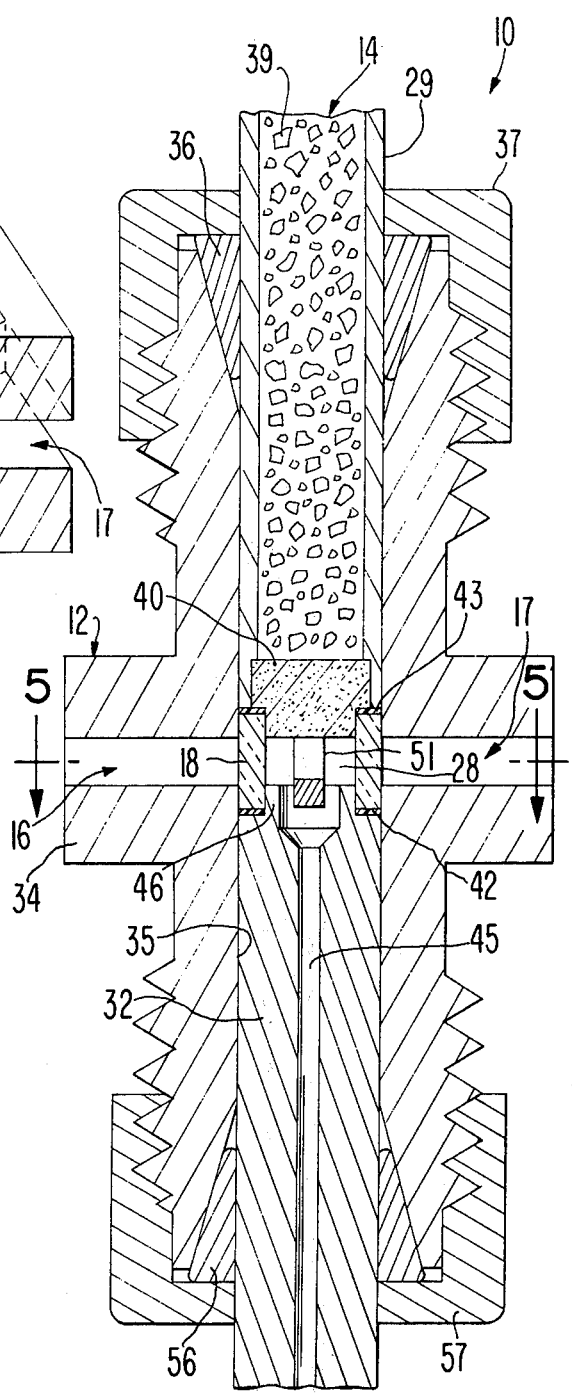
FIG. 2 is a longitudinal section of the flow cell of FIG. 1.
Figure 3:
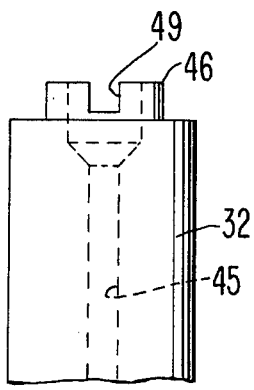
FIG. 3 is a side elevation of the bottom tube portion of the flow cell of FIGS. 1 and 2.
Figure 4:
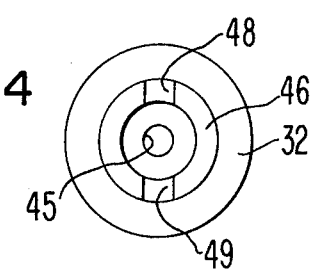
FIG. 4 is a top plan view of the bottom tube of FIG. 3.
Figure 8:
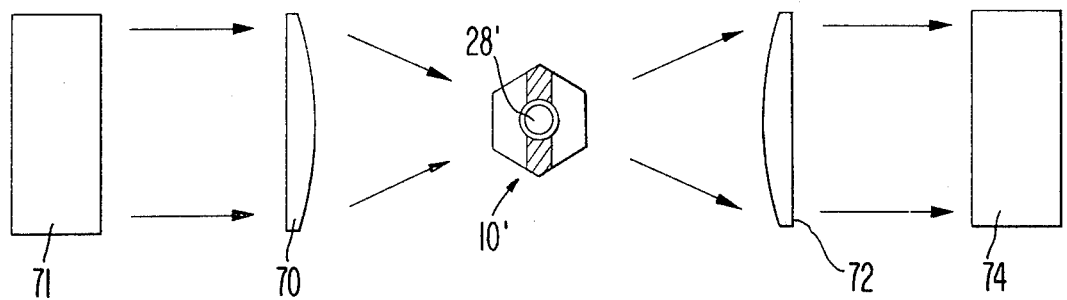
FIG. 8 is an optical schematic of an alternative embodiment of a liquid chromatography detector.

A schematic optical diagram of an alternative embodiment of the detector is shown in FIG. 8, in which the optical stops of a flow assembly 10' are omitted and convergence of the light rays is achieved solely through a lens system. In FIG. 8, a focusing lens 70 is provided to receive a collimated beam of light rays from a spectrophotometer 71 and to direct the rays through a flow cell portion 28', which is identical to the flow cell 28 except for the absence of optical stops. Light emitted through the flow cell 28' is received by a focusing lens 72 and directed to a photosensor 74. As in the previously described embodiment, all rays passing through the flow cell 28' are normal to the cylindrical window and pass through the center of the flow cell so that all are of equal length.

The dual flow cell 25 embodying the present invention is shown in detail in FIG. 9 of the drawings. A union 82 is provided into which two liquid chromatographic columns 84, 85 terminate. Each column enters the union from an opposite direction and terminates with a porous stainless steel plug 88, 89 respectively. Two pairs of cut out zones 90, 91 are provided axially spaced along the length of the union, each corresponding basically with the cut out portions 16, 17 of the union 12. Two cylindrical windows 92, 93 are received within a central passage 94 of the union, axially spaced by porous plugs 96, 97 and a spacer ring 98 and central exit zone 99. A perpendicular passage 100 extends through the wall of the union 82, at right angles to the central passage 94, from the exit zone 99. Each zone defined by the two cylindrical windows 92, 93 and the porous plugs 88, 96 and 89, 97 comprises an individual flow cell. Each of these cells receives liquid from one of the columns 84, 85. After passage through the cells, the liquid flows to the common exit zone 99 and thence through the outlet passage 100. Separate light beams are directed through the cut out zones 90, 91 and are separately detected. The separate beams are directed from a single source. A sample is passed in a solvent through one of the flow cells, and the solvent alone is passed through the other flow cell. The light outputs from both flow cells are detected, and the effects of the light source and solvent are factored out by suitable comparisons.

While the operations thereof of these different embodiments have been described in connection with the structures, it will be apparent in summary that in all embodiments the flow cell receives only convergent light rays directed normal to the cylindrical window of the flow cell, so that the light rays pass through the center of the flow cell. This assures that all light rays passing through the flow cell are essentially equal in length, are not refracted, and are gathered from a wide angle that provides high intensity and effectively averages any variations in light output throughout the area of the light source.

While preferred embodiments of the present invention have been described with particularity, it will be apparent that various modifications and alterations may be made therein without departing from the spirit and scope of the invention set forth in the appended claims.

What is claimed is:

1. For use in liquid chromatography, a detector comprising:
    a flow cell, said flow cell comprising a union connectable at one end to a column of a liquid chromatography apparatus, said union having a flow passage from said one end thereof to the other end thereof for effluent from said column, entrance and exit windows disposed in said union on diametrically opposite sides of said effluent flow passage, each of said windows being in the form of a cylinder segment providing a light acceptance angle of at least 45°;
    a light source emitting a collimated beam of light rays and having a light emitting area larger than the cross-sectional area of said passage;
    a lens for focusing all rays from said light source to said passage through said entrance window in paths normal to the cylindrical surface of said entrance window; and
    means for detecting light rays that emerge from said exit window.

2. The flow cell of claim 1 wherein said windows are formed of quartz.

3. The flow cell of claim 1 wherein connection of said union to said column is provided by ferrule and nut means.

4. The flow cell of claim 3 wherein said ferrule and nut means provides a compression-fitting connection.

* * * * *

UNITED STATES PATENT AND TRADEMARK OFFICE
CERTIFICATE OF CORRECTION

PATENT NO. : 4,006,990
DATED : February 8, 1977
INVENTOR(S) : MINER N. MUNK

It is certified that error appears in the above-identified patent and that said Letters Patent are hereby corrected as shown below:

Column 3, line 55: After "28" insert --to--.

Column 5, line 33: Delete "thereof".

Column 5, line 35: After "structures" insert --thereof--.

Signed and Sealed this

Thirteenth Day of December 1977

[SEAL]

Attest:

RUTH C. MASON
Attesting Officer

LUTRELLE F. PARKER
Acting Commissioner of Patents and Trademarks